United States Patent [19]

Monroe et al.

[11] Patent Number: 5,527,261

[45] Date of Patent: Jun. 18, 1996

[54] REMOTE HAND-HELD DIAGNOSTIC INSTRUMENT WITH VIDEO IMAGING

[75] Inventors: Richard A. Monroe, Liverpool; Robert J. Wood, Syracuse; Gregory E. Pasik, Auburn; Robert R. Huntley, Skaneateles Falls, all of N.Y.

[73] Assignee: Welch Allyn, Inc., Skaneateles Falls, N.Y.

[21] Appl. No.: 365,882

[22] Filed: Dec. 29, 1994

Related U.S. Application Data

[63] Continuation-in-part of Ser. No. 292,712, Aug. 18, 1994, abandoned.

[51] Int. Cl.$^6$ .................................................... A61B 1/00
[52] U.S. Cl. ......................... 600/109; 600/172; 600/176; 600/200; 348/65; 348/77
[58] Field of Search .............................. 348/65, 66, 77; 128/6, 9; 600/101, 109, 112, 160, 172, 176, 175, 179, 200

[56] References Cited

U.S. PATENT DOCUMENTS

| | | | |
|---|---|---|---|
| 4,604,992 | 8/1986 | Sato . | |
| 4,770,189 | 9/1988 | Shyu . | |
| 4,947,245 | 8/1990 | Ogawa et al. | 348/66 |
| 4,969,450 | 11/1990 | Chinnock et al. . | |
| 5,051,824 | 9/1991 | Nishigaki . | |
| 5,079,629 | 1/1992 | Oz | 128/6 |
| 5,239,984 | 8/1993 | Cane et al. . | |
| 5,251,025 | 10/1993 | Cooper et al. | 128/6 |
| 5,279,305 | 1/1994 | Zimmerman et al. . | |
| 5,363,839 | 11/1994 | Lankford | 128/9 |
| 5,368,015 | 11/1994 | Wilk . | |
| 5,418,566 | 5/1995 | Kameishi | 348/65 |
| 5,427,087 | 6/1995 | Ito et al. | 600/109 |
| 5,429,119 | 7/1995 | Griffin et al. | 600/200 |
| 5,429,502 | 7/1995 | Cooper et al. | 348/66 |

FOREIGN PATENT DOCUMENTS

| | | | |
|---|---|---|---|
| 3708131 | 9/1987 | Germany | 128/6 |

*Primary Examiner*—Angela D. Sykes
*Assistant Examiner*—Eric F. Winakur
*Attorney, Agent, or Firm*—Harris Beach & Wilcox

[57] ABSTRACT

A hand-held, fully remote diagnostic instrument having video capability is configured for any one of a number of clinical or industrial applications. The instrument has a casing that includes a hand-holdable body portion, a neck portion that extends from the body portion to a head portion that is formed of a back cover, a front cover, and a sealing gasket to form a fully soakable instrument. A circuit board assembly in the body portion contains video processing circuitry, and a flexible neck board which extends forward from the body portion through the neck portion of the casing to a head board located in the head portion of the casing. A solid state imager and a miniature lamp are disposed on the head board. The front cover contains an adjustable focus lens cell for focusing on the imager an image of a target in the lens cell's field of view. The instrument can be configured for various applications by installing front and back covers that are suited for a specific purpose. The instrument can thus be used, for example, as an otoscope, a dental camera, or a episcope. The instrument provides a monitor-ready standard format full color video signal to a remotely located monitor.

20 Claims, 3 Drawing Sheets

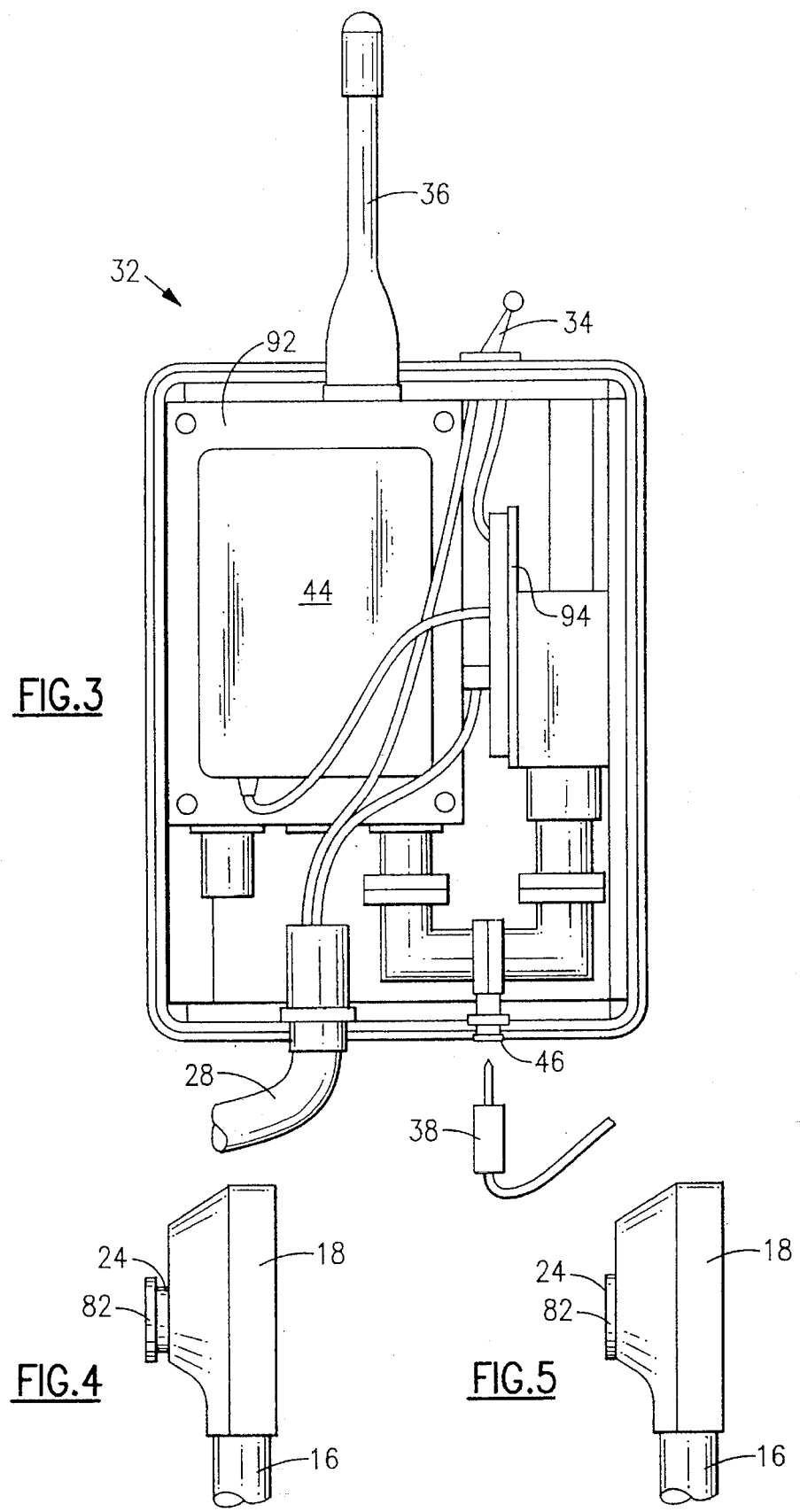

REMOTE HAND-HELD DIAGNOSTIC INSTRUMENT WITH VIDEO IMAGING

CROSS-REFERENCE TO RELATED APPLICATIONS

This application is a continuation-in-part of U.S. patent application Ser. No. 08/292,712, filed Aug. 18, 1994, now abandoned.

FIELD OF THE INVENTION

This invention relates to remote hand-held diagnostic instruments for either medical or industrial use, and is specifically directed to a remote device that employs a miniature video camera, a self-contained light source, and a video monitor. The instrument of the present invention can be a video probe, a video otoscope, a nasal scope, an epidural scope, or any one of a number of other remote diagnostic instruments used in conjunction with a video monitor. The instrument can also be designed for particular industrial inspections as, for example, examination of recessed equipment parts.

BACKGROUND AND SUMMARY OF THE INVENTION

Miniature video cameras have recently been incorporated into a wide variety of diagnostic instruments for producing a video image of a concealed target. Such instruments include, for example, laparoscopes, endoscopes, and borescopes. These prior devices require a separate source of illumination, and a fiber optic conduit to carry the light forward to illuminate the target.

In addition to this known video technology used in association with these relatively large diagnostic instruments, a number of smaller diagnostic instruments exist for the direct examination of tissue so that a medical practitioner can diagnose the health of such tissue by inspection of a particular patient. These types of diagnostic instruments include, for example, otoscopes, epidural scopes, and dental mirrors. Such instruments, however, require the practitioner to place the practitioner's eye near or on the instrument to conduct an inspection of the subject target while an image of the inspected tissue remains solely as a mental impression within the practitioner's memory. It is impossible with these conventional instruments to create any sort of hard copy record or permanent image of the object or target under inspection.

These limitations of the prior art have been overcome by the applicants. The present device incorporates these features and further adds the desired function of remote operation.

Accordingly, it is a principal object of this invention to provide a remote hand-held diagnostic instrument which includes a miniature video imager, focusing optics, and a light source, as well as necessary electronic circuitry to produce a monitor-ready standard video signal, so that an industrial inspector or medical practitioner can view a target on a standard video monitor.

It is another object of the present invention to provide a line of hand-held devices for different industrial and clinical purposes, the devices being generally common in style and function with a specific type of head cover.

A further object of this invention is to provide a hand-held instrument with adjustable focusing optics whose focal length can be changed manually such that a user of the instrument can hold the instrument and adjust its focus with one hand.

Yet another object of this invention is to utilize a single remote video diagnostic instrument in conjunction with a number of different video monitors positioned in different patient examination rooms or areas.

These and other objects are attained in accordance with the present invention wherein there is provided a remote hand-held diagnostic instrument with video imaging capability, and transmitter means for remotely transmitting and receiving a video signal. According to one aspect of this invention, the hand-held diagnostic instrument is provided with a casing or housing that has a hand-holdable body portion, a neck portion that extends forward from one end of the body portion, and a head portion situated on the distal end of the neck portion. The head portion is comprised of a back cover and a front cover. An arrangement of circuit boards is fitted into the body portion of the casing and contains video processing circuitry. A circuit board and/or flexible circuit member extends from the body portion through the neck portion of the casing and provides a receptacle for a head member which is positioned in the head portion of the casing. A solid-state imager, such as a CCD chip, is carried in the head member and is connected with the video processing circuitry on the circuit boards. A focusing lens assembly is carried in the front cover and focuses onto the imager an image of an object in the field of view of the lens assembly. The diagnostic instrument is connected to a remote transmitter capable of being suspended from a practitioner's belt or clothing. The transmitter transmits the video signal to a remotely located video monitor equipped with a receiver. In this manner, the practitioner is free to move without being limited by a hard-wire cable between the device and monitor.

In one preferred embodiment of the present device, the lens assembly includes a dual stage manually actuated mechanism for adjusting the focal length. A miniature lamp is carried on the head member displaced a small distance from the imager. The front cover is provided with a window or opening that directs illumination from the lamp into the field of view of the focusing lens assembly. A conduit or cable carries a processed standard format video signal to the portable transmitter. A battery pack contained in the transmitter, provides forward power to the lamp, imager, and image processing circuitry. The picture on the monitor is an image of the target as viewed by the imager in the instrument. This picture can be digitized and captured, for example, for storage in a magnetic memory of a small computer. A hard or paper copy of the image can then be generated.

The head cover and neck incorporate an air tight seal allowing the device to be disinfected after a clinical use. Disposable transparent sterile sheaths can be employed to cover the head and neck to prevent contamination from a patient's body fluids. In addition, the front and back covers of the head portion can be detachable and interchangeable with covers, optical assemblies, and air tight seals of another style to convert the instrument, for example, from a nasal probe to an otoscope.

BRIEF DESCRIPTION OF THE DRAWING

Further objects of the present invention together with additional features contributing thereto and advantages accruing therefrom will be apparent from the following description of a preferred embodiment of the invention which is shown in the accompanying drawing, wherein:

FIG. 3 is an elevation view of a video transmitter used in conjunction with the present invention;

FIG. 4 is a side elevation view of the head portion of the present diagnostic instrument showing the lens cell thereof in an extra-oral position; and FIG. 5 is a view similar to FIG. 4 showing the lens cell of the head portion of the present diagnostic instrument in an intra-oral position.

DETAILED DESCRIPTION OF A PREFERRED EMBODIMENT

Figure 1:
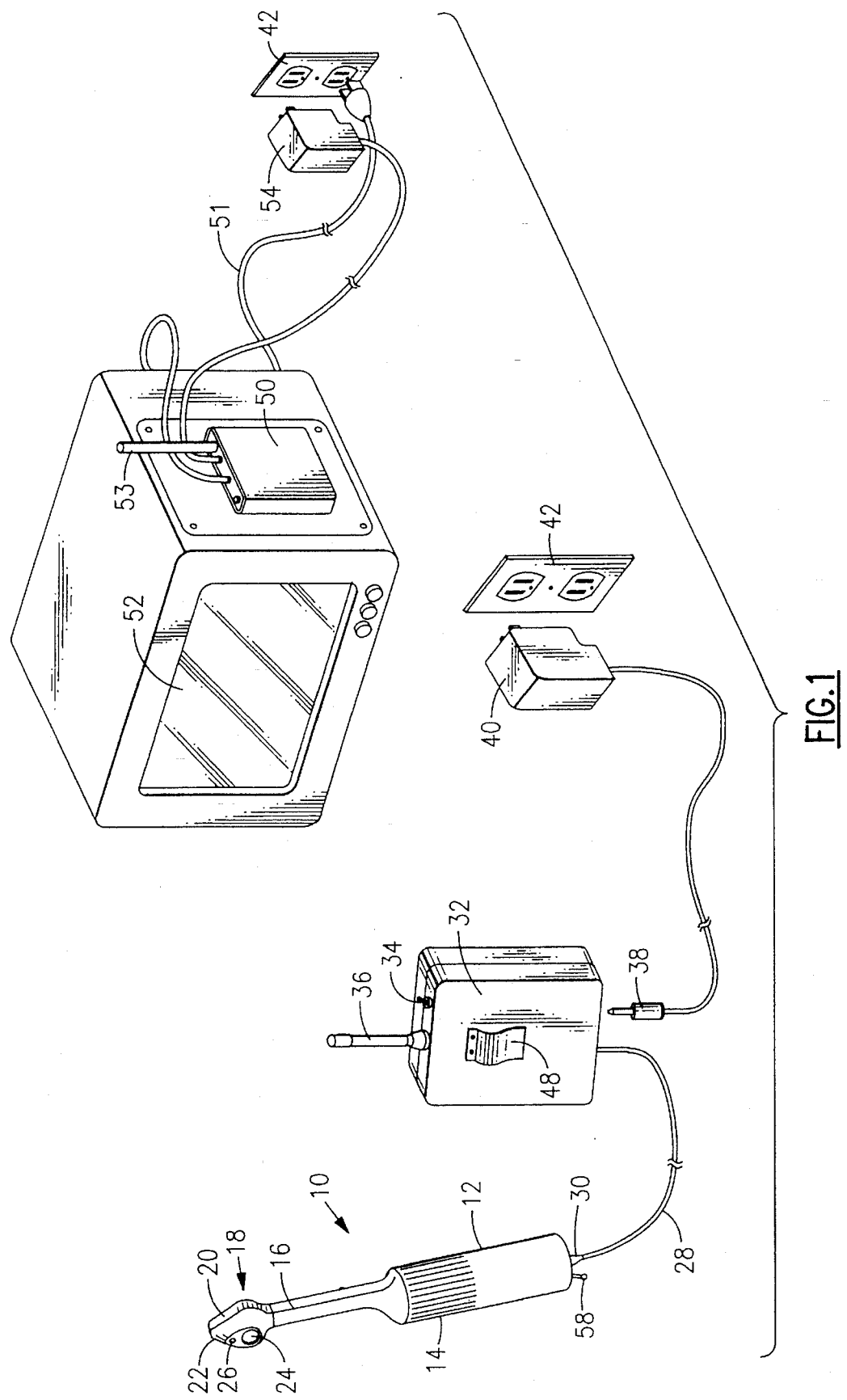
FIG. 1 is a perspective view of a remote hand-held multipurpose diagnostic instrument in combination with an associated power supply and monitor, the device of FIG. 1 being configured as a variable focus dental camera.

With reference now to the drawing and initially to FIG. 1, a video dental instrument 10 is shown to illustrate the principles of this invention. The instrument 10 has a hand-holdable casing 12 with a generally cylindrical body portion 14, a narrow elongated neck portion 16 that extends from an upper end of the body portion 14, and a head portion 18. The head portion is substantially oval in shape, and has a back cover 20 and a front cover 22. An adjustable lens cell 24 is situated on the head 18 in the front cover 22, and a lamp window 26 is provided on the cover 22 above the lens cell 24. Processed video signals are carried on a cable 28, having a strain relief 30, to a portable video signal transmitter 32. The transmitter 32 is provided with on/off toggle switch 34 and a transmission antenna 36. A charging plug 38 is connected to a first power supply transformer 40. As illustrated in FIG. 1, the power supply transformer 40 is of the type adapted to be plugged into a common wall outlet 42 connected to the mains. As shown in FIG. 3, the transmitter 32 includes a rechargeable battery pack 44 which is charged by inserting the charging plug 38 into a charging port 46. With reference again to FIG. 1, it is shown that the transmitter 32 is provided with a clip 48. In this manner, the fully charged transmitter 32 may be clipped to a practitioner's belt or pocket. With use of the dental instrument 10 and transmitter 32, the practitioner is free to move about the patient without the constraints associated with a transmission cable. The transmitter 32 transmits a video signal to a remotely positioned video receiver 50 which is hard-wired to a video monitor 52. The receiver 50 is provided with a receiving antenna 53 while the receiver 50 is powered by a second power supply transformer 54. The video monitor is powered by a monitor plug 51. As illustrated in FIG. 1, the power supply transformer 54 is also of the type adapted to be plugged into the common wall outlet 42 connected to the mains. The range of the instrument 10 is on the order of 100 feet. It is thus contemplated that a single instrument 10 may be used in conjunction with a number of monitors 52. For example, a video monitor may be positioned near each of a dentist's chairs so that a patient in the chair, the dentist and an assistant all have a view of the image on the monitor. In this manner, the dentist may circulate among patients in different chairs while carrying only one instrument 10. In the proposed medical applications of the instrument 10, a doctor may similarly carry one instrument and examine a number of different patients in different examining rooms each equipped with a monitor 52.

Figure 2:
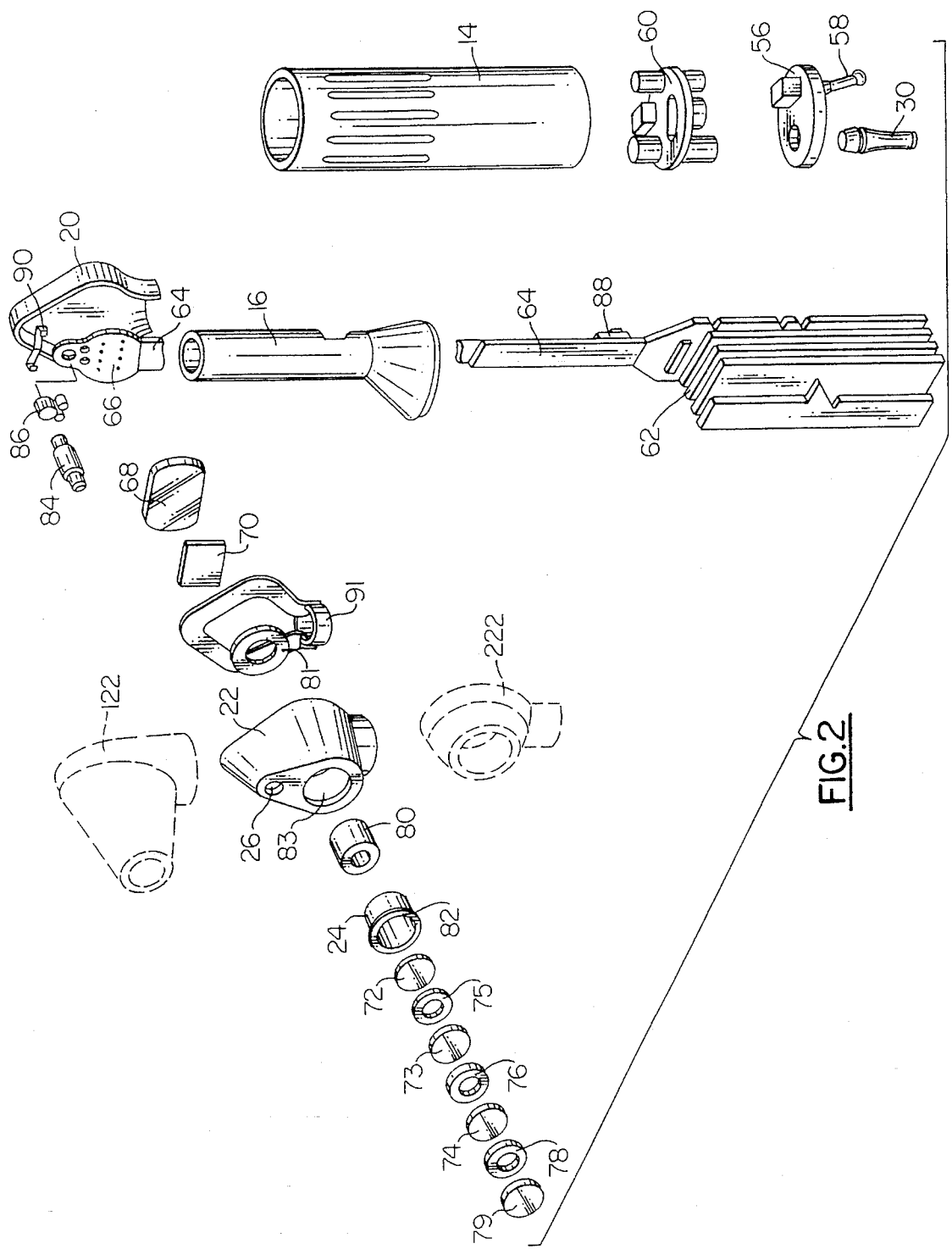
FIG. 2 is an exploded assembly view of the embodiment of the present device illustrated in FIG. 1, FIG. 2 also showing in phantom alternative otoscope and episcope head covers.

Details of the instrument 10 and a preferred embodiment of adjusting the optics are shown in the exploded assembly view of FIG. 2. The body portion 14 is closed off at its lower end by an end cap 56 which seats the strain relief 30 and carries an on-off system switch 58, also shown in FIG. 1. The on-off system switch 58, in conjunction with the transmitter switch 34, FIG. 1, is for activating or deactivating the hand-held scope and the transmitter portion of the video system. An end printed circuit board 60 is in the form of a disk positioned adjacent the end cap 56. A stack of circuit boards 62, located within the body portion 14, carries video processing circuitry. A flexible circuit board 64 carrying flexible circuitry extends longitudinally through the neck portion 16 of the casing 12 and connects to a head board 66 which is contained within the head 18.

A miniature CCD imager chip 68 is mounted on the head board 66 with an infrared filter 70 positioned over the imager chip 68. The lens cell 24 is generally cylindrical and carries three objective lenses 72, 73, and 74. A first spacer 75 is situated between lenses 72 and 73 while a second spacer 76 is similarly positioned between lenses 73 and 74. An aperture ring 78 is positioned in front of the lens 74 and a plano lens 79 is located over the aperture ring 78. A slide 80, preferably formed of a non-stick substance such as TEFLON, employed to move the lens cell 24 between two focal lengths described later in conjunction with FIGS. 4 and 5. The lens cell 24 is retained within the instrument head by a stop ring 81 and a face ring 82 formed on the front of the lens cell. A fluid tight seal is thereby provided between the lens cell 24 and an opening 83 in the front cover 22.

A miniature lamp 84 is fitted into a lampholder 86 mounted at one end of the head board 66. Activation of the lamp 84 is independently controlled by an on-off lamp switch 88. An electrical contact 90 fitted to the head board 66 is spring biased against a contact on the lamp 84. The lamp 84 is positioned to direct illumination forward through the window 26 in the front cover 22 and into the field of view of the lens cell 24. The lamp 84 is preferably but not limited to a 2.5 volt miniature halogen lamp having low heat output to prevent any discomfort to the patient. The front cover 22 can be removed when necessary, for example, to replace the lamp 84. Thereafter, the front cover 22 can easily be reassembled back in place on the neck portion 16 and back cover 20.

A head sealing gasket 91 is provided to form a fluid-tight seal between the front cover 22, the rear cover 20 and the neck portion 16. The gasket 91 allows the head portion 18 to be fully soakable for disinfection purposes without causing moisture damage to the components contained therein.

The instrument 10 shown here is a dental camera, and the front and rear covers 22 and 20 of the head portion 18 are somewhat teardrop-shaped. This shape is conveniently placed in a dental patient's mouth to permit the dentist to see the patient's teeth and gums on the monitor 52. The instrument, however, can be easily configured as another hand-held instrument simply by installing a different front cover, back cover, and seal. Here, as shown in phantom, an otoscope front cover 122 has a conic nose, while an alternate front cover 222 for an episcope has a flattened frustoconic nose. Each of the alternative covers has a corresponding rear cover (not shown) and focusing optics. The focusing optics can either be adjustable or fixed. In addition, the alternative front covers 122 and 222 also include means for directing light from the lamp 84 forward into the field of view of the associated focusing optics. This illumination may be supplied directly from a lamp or through a fiber bundle, or indirectly by use of a reflector.

A disposable sanitary sheath or cover can be placed over the neck and head portions 16 and 18 to prevent a patient's body fluids form contacting and contaminating the instrument. The sheath is optically transparent at least on the portion that overlies the front cover 22. In addition, the various alternative configurations have focusing lens assemblies of a viewing angle and aperture as need for a specific application. Each of the various configurations, however, employs a common CCD imager and a common electrical circuit. The image processing circuitry preferably converts raw video information from the imager 68 into a monitor ready standard format signal suitable for the particular monitor 52. This can be a standard NTSC, PAL, or Secam color video signal.

With reference again to FIG. 3, it is shown that the transmitter 32 includes a transmission unit 92. The hard-wiring between the transmission unit 92 the battery pack 44, the toggle switch 34, and the charging port 46 is also illustrated in FIG. 3. The transmitter 32 also includes a video converter 94 which, in this preferred embodiment, modulates raw Y and C video output from the circuit boards 62 to a standard composite video signal. This composite signal is then demodulated to produce a full color composite signal on the monitor 52. The control circuitry for the various components of the transmitter 32 is contained in the circuit boards 62 which are housed within the body handle 14. The arrangement of components within the transmitter 32 thus allows for a considerably compact multi-functional unit.

Referring again to FIGS. 4 and 5, it is shown that the head 18 of the instrument 10 includes two focusing positions. FIG. 4 illustrates the lens cell 24 extended to an intra-oral position. In this position, the range of field of the imaging optics is approximately ¼ inch to about 1 and ¼ inch. The intra-oral position is thus suited for close-up imaging of, for example, a whole tooth, a part of a tooth or gum line. FIG. 5 shows the lens cell 24 retracted into an extra-oral position. In this position, the range of field of the imaging optics is approximately 6 to 8 inches. The intra-oral position is employed to provide a full mouth image from a location exterior to the mouth cavity. The lens cell 24 is moved between the extra-oral and intra-oral positions, respectively, by simply depressing the cell into the head 18 or by the practitioner placing his finger nails under the face ring 82 and extending the lens cell 24 into the intra-oral position shown in FIG. 4.

While this invention has been described in detail with reference to a certain preferred embodiment and alternative head cover configurations, it should be appreciated that the present invention is not limited to that precise embodiment or particular cover configurations. Rather, in view of the present disclosure which describes the current best mode for practicing the invention, many modifications and variations would present themselves to those of skill in the art without departing from the scope and spirit of this invention, as defined in the following claims.

We claim:

1. A remote hand-held diagnostic instrument comprising:
    a hand-holdable casing including a body portion, a neck portion extending distally from the body portion, and a head portion formed with a front cover, a back cover, and a sealing means for providing a fluid seal between said front and back covers;
    circuit board means and video processing circuitry within said casing, said circuit board means including a flexible board extending from said body portion through said neck portion of said casing and having a head member positioned in the head portion of said casing;
    a solid state imager affixed within said head member and in circuit communication with said video processing circuitry;
    focusing means carried on said front cover for focusing onto the imager an image of an object in its field of view;
    a lamp carried on said head member;
    means in said front cover for directing illumination from said lamp into said field of view;
    electrical conduit means for carrying power to said video processor circuitry and to said lamp and for carrying from said video processor circuitry a video signal representing said object in said field of view; and
    transmitter means for receiving said video signal from said electrical conduit means and remotely transmitting said video signal.

2. The remote hand-held diagnostic instrument according to claim 1 wherein said front cover, back cover and sealing means are detachably connected to said head portion.

3. The remote hand-held diagnostic instrument according to claim 1 wherein said focusing means includes means for manually adjusting a focal length of a lens cell.

4. The remote hand-held diagnostic instrument according to claim 3 wherein said lens cell has two focus positions relative to said head portion.

5. The remote hand-held diagnostic instrument according to claim 4 wherein one of said two focus positions is an intra-oral position having a range of field of approximately ¼ inch to 1 and ¼ inches.

6. The remote hand-held diagnostic instrument according to claim 4 wherein one of said two focus positions is an extra-oral position having a range of field of approximately 6 inches to 8 inches.

7. The remote hand-held diagnostic instrument according to claim 1 wherein said front cover is an otoscope cover having a conic nose in which a lens cell is located.

8. The remote hand-held diagnostic instrument according to claim 1 wherein one of said front and back covers is an episcope cover having a frustoconic face.

9. The remote hand-held diagnostic instrument according to claim 1 wherein said video processor circuitry on said circuit board means includes means for outputting to said conduit means a standard monitor-ready full color video signal.

10. The remote hand-held diagnostic instrument according to claim 1 wherein said solid state imager is detachably connected to the head member of said flexible board.

11. A video diagnostic system comprising
    a) a remote hand-held diagnostic instrument including:
        a hand-holdable casing including a body portion, a neck portion extending distally from the body portion, and a head portion formed with a front cover, a back cover, and sealing means for providing a fluid-seal between said front and back covers;
        circuit board means and video processing circuitry within said casing, said circuit board means including a flexible board extending from said body portion through said neck portion of said casing and having a head member positioned in the head portion of said casing;
        a solid state imager affixed within said head member and in circuit communication with said video processing circuitry;
        focusing means carried on said front cover for focusing onto said solid state imager an image of an object in its field of view;

a lamp carried on said head member;

means in said front cover for directing illumination from said lamp into said field of view;

electrical conduit means for carrying power to said video processor circuitry and to said lamp and for carrying from said video processor circuitry a video signal representing said object in said field of view; and transmitter means for receiving said video signal from said electrical conduit means and remotely transmitting said video signal, and b) at least one video monitor having a receiver for receiving said video signal while said remote hand-held diagnostic instrument is being used at a distant location.

12. The video diagnostic system according to claim 11 wherein said front cover, back cover, and sealing means are detachably connected to said head portion.

13. The video diagnostic system according to claim 11 further comprising a lens cell, and wherein said focusing means includes means for manually adjusting a focal length of said lens cell.

14. The video diagnostic system according to claim 13 wherein said lens cell has two focus positions relative to said portion.

15. The video diagnostic system according to claim 14 wherein one of said two focus positions is an intra-oral position having a range of field of approximately ¼ inches to 1 and ¼ inches.

16. The video diagnostic system according to claim 14 wherein one of said two focus positions is an extra-oral position having a range of field of approximately 6 inches to 8 inches.

17. The video diagnostic system according to claim 11 wherein said front and back covers are otoscope covers having a conic nose in which said lens cell is located.

18. The video diagnostic system according to claim 11 wherein one of said front and back covers is an episcope cover having a frustoconic face.

19. The video diagnostic system according to claim 11 wherein said video processor circuitry on said circuit board means includes means for outputting to said conduit means a standard monitor-ready full color video signal.

20. The video diagnostic system according to claim 11 wherein said solid state imager is detachably connected to the head member of said flexible board.

* * * * *